United States Patent [19]

Reifschneider et al.

[11] 4,444,764

[45] Apr. 24, 1984

[54] PHOSPHORUS ESTERS OF ALKYLCYCLOALKYL-5-PYRIMIDINOLS AND CONTROL OF CORN ROOTWORM AND WESTERN SPOTTED CUCUMBER BEETLE WITH THEM

[75] Inventors: Walter Reifschneider, Walnut Creek, Calif.; Larry L. Larson, Omaha, Nebr.

[73] Assignee: The Dow Chemical Company, Midland, Mich.

[21] Appl. No.: 246,500

[22] Filed: Mar. 23, 1981

Related U.S. Application Data

[63] Continuation-in-part of Ser. No. 64,218, Aug. 6, 1979, abandoned, and Ser. No. 172,593, Jul. 28, 1980, abandoned.

[51] Int. Cl.³ .................... A01N 57/16; A01N 57/24; C07F 9/65
[52] U.S. Cl. .................. 424/200; 544/243; 544/298
[58] Field of Search ............. 544/243, 298; 424/200

[56] References Cited

U.S. PATENT DOCUMENTS

| | | | |
|---|---|---|---|
| 4,012,506 | 3/1977 | Balke et al. | 424/200 |
| 4,127,652 | 11/1978 | Maurer et al. | 424/200 |
| 4,254,113 | 3/1981 | Maurer et al. | 424/200 |
| 4,261,983 | 4/1981 | Maurer et al. | 424/200 |
| 4,325,948 | 4/1982 | Maurer et al. | 424/200 |

Primary Examiner—Diana G. Rivers

[57] ABSTRACT

Compounds of the formulas:

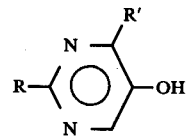

and

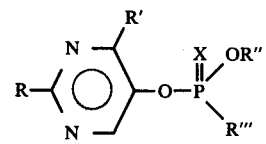

wherein R is alkylcycloalkyl having 4 to 6 carbon atoms; R' is hydrogen, alkyl or alkylthio of 1 to 3 carbons; R" is alkyl having 1 to 4 carbon atoms; X is oxygen or sulfur; and R'" is alkyl of 1 to 2 carbons, alkoxy, alkylthio or monoalkylamino, each with 1 to 4 carbon atoms, or phenyl. The novel 1-alkylcycloalkyl pyrimidinols are used in preparing the phosphate compounds which are highly useful corn rootworm control agents and are particularly valuable when applied to the soil, but are also useful applied to foliage of corn. Especially good control is obtained of corn rootworm. The compounds are conveniently applied in the form of a composition containing a pesticidal carrier such as an inert solvent or a finely divided inert solid in which case the composition is preferably granulated. An effective application rate is in the range of about 0.1 to about 5 pounds per acre when soil incorporated, and about 0.5 to about 2000 ppm for foliar applications.

18 Claims, No Drawings

PHOSPHORUS ESTERS OF ALKYLCYCLOALKYL-5-PYRIMIDINOLS AND CONTROL OF CORN ROOTWORM AND WESTERN SPOTTED CUCUMBER BEETLE WITH THEM

This application is a continuation-in-part of application Ser. No. 064,218 filed Aug. 6, 1979, and application Ser. No. 172,593 filed July 28, 1980, both now abandoned.

BACKGROUND OF THE INVENTION

1. Field of the Invention

The invention relates to novel pyrimidinols which may be employed in the preparation of highly useful pyrimidinyl phosphates, phosphorothioates and phosphorodithioates which are particularly effective corn rootworm and western spotted cucumber beetle control agents when applied to the soil of corn crops.

2. Description of Prior Art

It has long been a desired objective in the art to provide an insecticide effective and useful in the control of corn rootworm. It is also desirable to provide an insecticide with systemic activity whereby the insecticide can be soil incorporated and to have the insecticide taken up effectively by growing crops and delivered to the point of attack by insects by systemic activity or translocation within the plant.

Phosphate esters similar to the present compounds are described in U.S. Pat. No. 4,012,506, which discloses compounds such as O,O-diethyl O-(2-cyclopropyl-4-methyl-6-pyrimidinyl) thiophosphate. The patented compounds are made from 6-pyrimidinols whereas the present compounds are prepared from 5-pyrimidinols. The present compounds have surprisingly greater activity and effectiveness than do the corresponding patented compounds with similar ring substituents, particularly against corn rootworm by application of the active ingredient to the soil of a crop such as corn.

Other pyrimidinyl phosphate esters became recently known to the art as, for example, U.S. Pat. No. 4,127,652, German OLS No. 28 35 492, and in the copending application Ser. No. 928,665 filed July 26, 1978.

SUMMARY OF THE INVENTION

The novel, highly useful compounds of the invention are those of the following formulas:

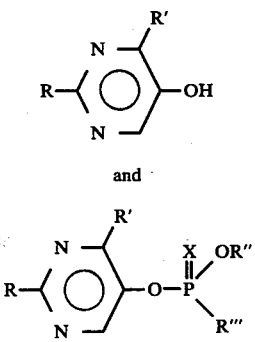

wherein R is alkylcycloalkyl having 4 to 6 carbon atoms; R' is hydrogen, alkyl having 1 to 4 carbon atoms or alkylthio of 1 to 3 carbons; R'' is alkyl having 1 to 4 carbon atoms; X is oxygen or sulfur; and R''' is alkyl of 1 to 2 carbons, alkoxy, alkylthio or monoalkylamino, each with 1 to 4 carbon atoms, or phenyl.

The novel 2-alkylcycloalkyl pyrimidinols are used in preparing the phosphate compounds which are highly useful corn rootworm and western spotted cucumber beetle control agents and are particularly valuable when applied to the soil. The compounds are conveniently applied in the form of a composition containing a pesticidal carrier such as an inert solvent or a finely divided inert solid in which case the composition is preferably granulated. An effective application rate is in the range of about 0.1 to about 5 pounds per acre when soil incorporated.

Compositions containing from about 0.05 to about 20 percent by weight of the phosphate ester compounds are highly useful in the control of corn rootworm and western spotted cucumber beetle when applied to the soil. Useful concentrates contain from about 5 to about 98 percent by weight active ingredient. Soil application rates are primarily in the range of about 0.1 to about 2 pounds of active ingredient per acre.

The phosphate ester compounds are largely somewhat viscous oils, or, solids melting below 100° C., which are rather readily soluble in many common organic solvents such as xylene or acetone or petroleum distillates and of very low solubility in water.

The novel 2-alkylcycloalkyl-5-pyrimidinol intermediates may be prepared by the following route: an appropriate alkylcycloalkyl nitrile is converted by the method of Pinner (Org. Synth. Collect. Vol. I, page 5) to the alkylcycloalkanecarboximidamide which is then allowed to react with N-(3-(dimethylamino)-2-ethoxy-2-propenylidene)-N-methylmethanaminium perchlorate (Z. Arnold, 1973, Collect. Czech. Chem. Commun. 38, 1168-72) in the presence of sodium methoxide. The conversion to the 2-alkylcycloalkyl-5-pyrimidinols may be accomplished by heating the resulting ethyl ether with sodium ethylmercaptide in dimethylformamide (DMF). Alternatively, a Vilsmeier reagent may be prepared from DMF and phosgene in methylene chloride. One can then add methoxyacetaldehyde dimethylacetal, reflux for 12–20 hours, cool to 0°, add the appropriate cycloalkanecarboximidamide and slowly add sodium methoxide in methanol. After removal of methylene chloride and reflux for two hours the desired 2-alkylcycloalkyl-5-methoxypyrimidine is obtained. The methyl ether is cleaved to the corresponding pyrimidinol by any of several methods and as with sodium ethylmercaptide in DMF, sodium cyanide in dimethylsulfoxide (DMSO) or potassium hydroxide in glycol.

To obtain an alkylcycloalkyl-4-methyl-5-pyrimidinol, methyl methoxyacetate was condensed to the corresponding acetoacetic ester with the aid of potassium t-butoxide. The alkylcycloalkanecarboximidamide was added and the mixture heated to reflux. The resulting 2-alkylcycloalkyl-5-methoxy-6-methoxymethyl-4-pyrimidinol was treated with phosphorus oxychloride to provide the 4-chloro derivative which was reduced with zinc in 1 N aqueous sodium hydroxide to 2-alkylcycloalkyl-5-methoxy-4-methylpyrimidine. Cleavage as previously described gave the 2-alkylcycloalkyl-4-methyl-5-pyrimidinol.

To prepare a 4-alkylthio-2-alkylcycloalkyl-5-pyrimidinol, methyl methoxyacetate is condensed with ethyl formate with the aid of potassium tert.-butoxide. The alkylcycloalkanecarboximidamide is then added to the resulting product and the mixture is heated under reflux. The 2-alkylcycloalkyl-5-methoxy-4-pyrimidinol is obtained and converted to 4-chloro-2-alkylcycloalkyl-5-methoxypyrimidine by phosphorus oxychloride. The chlorine compound is then allowed to react with a sodium alkylmercaptide and the resulting 4-alkylmercapto-2-alkylcycloalkyl-5-methoxypyrimidine is cleaved to the desired 4-alkylthio-2-alkylcycloalkyl-5-pyrimidinol by any of the methods previously described.

The phosphorus derivatives of the pyrimidinols were prepared using the appropriate phosphorus chloride, potassium carbonate as hydrogen chloride acceptor and acetonitrile as solvent.

The reaction may be carried out conveniently in any inert organic liquid such as benzene, toluene, xylene, chlorobenzene, petroleum ether, methylene chloride, chloroform, carbon tetrachloride, ethers, such as diethyl ether, dibutyl ether and dioxane, ketones, such as acetone, methyl ethyl ketone, methyl isopropyl ketone or methyl isobutyl ketone, and nitriles, such as acetonitrile and propionitrile.

Also employed is an acid binding agent or acceptor selected from alkali carbonates, alkali hydroxides, and alcoholates such as sodium carbonate, potassium carbonate, sodium or potassium methylate or ethylate and aliphatic, aromatic or heterocyclic amines, for example, triethylamine, trimethylamine, dimethylaniline, dimethylbenzylamine and pyridine.

The reaction temperature can be selected from a rather large range between about 0° to about 100° C., preferably about 20° to about 60° C. The reaction is generally carried out under ambient atmospheric pressure conditions.

The amounts of the reagents to be employed are not critical, some of the desired products being obtained when employing any proportion of the reactants. In the preferred method of operation, good results are obtained when employing substantially equimolecular proportions of the pyrimidinol and phosphorochloridate, phosphoroamidochloridothioate, phosphonochloridothioate, phosphorochloridodithioate or phosphorochloridothioate. The reaction takes place smoothly at the temperature range from 0° to 100° C. with the production of the desired product and chloride by-product. In carrying out the reaction, the reactants are mixed and contacted together in any convenient fashion, and the resulting mixture maintained for a period of time in the reaction temperature range to complete the reaction. Following the completion of the reaction, the reaction mixture is washed with water and any organic reaction medium removed by distillation under reduced pressure to obtain the desired product as a residue. This product can be further purified by conventional procedures such as washing with water and dilute aqueous alkali metal hydroxide, solvent extraction and recrystallization.

The phosphorochloridates, phosphoroamidochloridothioates, phosphonochloridothioates or phosphorochloridothioates which are employed as intermediates are prepared according to methods well known in the art. In the case of the dithioates, the intermediate may be prepared in several steps by reacting PCl$_3$ with the appropriate alkylsulfenylchloride in the presence of sulfur dioxide to obtain S-alkyl phosphorodichloridothioate which is then reacted with phosphorous pentasulfide to obtain S-alkyl phosophorodichloridodithioate. This latter compound is then reacted with ethanol in the presence of an acid acceptor such as triethylamine, producing however a mixture of the desired product, O-ethyl S-alkyl phosphorochloridodithioate, starting material and a by-product, O,O-diethyl S-alkyl phosphorodithioate, which mixture must be resolved. More preferably the ammonium salt of O,O-diethyl dithiophosphoric acid is alkylated with the appropriate alkyl bromide to give the S-alkyl O,O-diethyl phosphorodithioate which is then treated with sodium hydrogen sulfide or with sodium ethylmercaptide to give the sodium salt on cleaving of one of the ethyl groups. The sodium salt is then reacted with phosphorous pentachloride to yield the desired O-ethyl S-alkyl phosphorochloridodithioate.

The following examples further illustrate the invention.

Example 1

1-Methylcyclopropanecarboximidamide, monohydrochloride

A mixture of 48.3 g of 1-methylcyclopropylcyanide (D. Gotkis and J. B. Cloke, J. Am Chem. Soc. 56, 2710–2712 (1934)) and 35 ml of absolute ethanol was cooled to 0° and approximately 30 g of hydrogen chloride was introduced in such a rate that the temperature of the reaction mixture did not raise above 5° C. After the addition was complete, the cooling bath was removed and the mixture stirred at room temperature overnight. Vacuum was then applied to the reaction mixture to remove as much excess hydrogen chloride as possible. To the oily viscous residue 25 ml of absolute ethanol was added followed by a dropwise addition of a solution of approximately 20 g of ammonia in 125 ml of absolute ethanol. The mixture was kept below 20° C. by cooling. The resulting mixture was stirred at room temperature for three hours, the ammonium chloride removed by filtration and the filtrate concentrated under vacuum. The solid residue was recrystallized from isopropanol/ether to yield 66.7 g (83%) of white crystals, m.p. 185°–187° C.

Analysis: Found: C, 44.13; H, 8.06; N, 20.80. Calcd. for $C_5H_{10}N_2.HCl$: C, 44.61; H, 8.24; N, 20.81

Example 2

5-Ethoxy-2-(1-methylcyclopropyl)pyrimidine

To a stirred mixture of 60.3 g of 1-methylcyclopropanecarboximidamide, monohydrochloride, 121 g of N-(3-(dimethylamino)-2-ethoxy-2-propenylidene)-N-methylaminium perchlorate (Z. Arnold, Collect. Czech. Chem. Commun. 38, 1168–1172 (1973)) and 100 ml of methanol was added dropwise a sodium methoxide solution, prepared from 31 g of sodium and 600 ml of methanol. After the addition was complete, the mixture was heated under reflux for three hours and was then concentrated under vacuum. The residue was taken up in water and extracted twice with ether. The ether extract was dried over anhydrous sodium sulfate, the ether removed in a rotary evaporator and the residual oil distilled in a Kugelrohr (bath temperature 65° C., pressure 0.2 mm) to give a colorless oil, RI(25°)=1.5162. Yield, 66.7 g (83%).

Analysis: Found: C, 67.24; H, 8.00; N, 15.74. Calcd. for $C_{10}H_{14}N_2O$: C, 67.38; H, 7.92; N, 15.72.

The 5-ethoxypyrimidine listed in the following TABLE I was prepared in essentially the same manner.

TABLE I

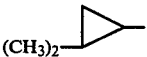

| Example | R | B.p. °C./mm RI (25° C.) |
|---|---|---|
| 3 | (CH₃)₂-▷- | 65/0.2* 1.5100 |

*Distilled in a Kugelrohr. Temperature of the airbath is given.

Example 4

2-(1-Methylcyclopropyl)-5-pyrimidinol

A mixture of 64.2 of 5-ethoxy-2-(1-methylcyclopropyl)pyrimidine, 67.5 g of sodium ethylmercaptide and 440 ml of dimethyl formamide was stirred, heated and the formed diethyl sulfide removed via a Dean Stark trap. After heating under reflux for two hours, the dimethyl formamide was removed as far as practical by distillation under vacuum. The residue was taken up in water and the resulting solution acidified with glacial acetic acid. The product precipitated, was collected by filtration, washed with water, dried in air and recrystallized from ethyl acetate to yield 45.6 g (84%) of white crystals, m.p. 168°–170° C.

Analysis: Found: C, 63.78; H, 6.74; N, 18.53. Calcd. for $C_8H_{10}N_2O$: C, 63.98; H, 6.71; N, 18.65.

The 5-pyrimidinol listed in the following TABLE II was prepared in essentially the same manner as described above.

TABLE II

| Example | R | M.p. °C. | % Yield | Analysis Calcd. | Found |
|---|---|---|---|---|---|
| 5 | (CH₃)₂-▷- | 159–161 | 73 | C 65.83<br>H 7.37<br>N 17.06 | 65.97<br>7.24<br>16.96 |

Example 6

Phosphorothioic acid: O,O-dimethyl O-(2-(1-methylcyclopropyl)-5-pyrimidinyl) ester A mixture of 7.5 g of 2-(1-methylpropyl)-5-pyrimidinol, 8.0 g of O,O-dimethyl phosphorochloridothioate, 60 ml of acetonitrile and 10 g of finely powdered potassium carbonate was stirred for 90 minutes. The salts were removed by filtration, the filtrate concentrated under vacuum, the residual oil taken up in ether, the ether solution washed twice with 2 percent aqueous sodium hydroxide, once with saturated sodium chloride solution and dried over anhydrous sodium sulfate. The ether was removed in a rotary evaporator leaving 11.7 g (86%) of a colorless oil. RI(25°)=1.5274.

Analysis: Found: C, 43.52; H, 5.62; N, 10.18. Calcd. for $C_{10}H_{15}N_2O_3PS$: C, 43.79; H, 5.51; N, 10.22.

Example 7

Phosphorothioic acid: O,O-diethyl O-(2-(1-methylcyclopropyl)-5-pyrimidinyl) ester A mixture of 7.5 g of 2-(1-methylcyclopropyl)-5-pyrimidinol, 10 g of finely powdered potassium carbonate, 60 ml of acetonitrile and 9.4 g of O,O-diethyl phosphorochloridothioate was stirred for 90 minutes. The salts were then removed by filtration and the filtrate concentrated under vacuum. The residual oil was taken up in ether, the ether solution washed twice with 2 percent aqueous sodium hydroxide, once with saturated sodium chloride solution and dried over anhydrous sodium sulfate. The ether was removed in a rotary evaporator leaving 13.8 g (92%) of a colorless oil. RI(25°)=1.5150.

Analysis: Found: C, 47.69; H, 6.40; N, 9.26. Calcd. for $C_{12}H_{19}N_2O_3PS$: C, 47.67; H, 6.33; N, 9.27.

In a like manner the following diethyl ester was prepared:

TABLE IV

| Example | R | M.p. °C. RI (25°) | % Yield | Analysis Calcd. | Found |
|---|---|---|---|---|---|
| 5 | (CH₃)₂-▷- | 1.5100 | 88 | C 49.35<br>H 6.69<br>N 8.86 | 49.65<br>6.60<br>8.56 |

Example 9

Phosphorodithioc acid: O-ethyl O-(2-(1-methylcyclopropyl)-5-pyrimidinyl) S-propyl ester A mixture of 5.0 g of 2-(1-methylcyclopropyl)-5-pyrimidinol, 7 g of finely powdered potassium carbonate, 50 ml of acetonitrile and 7.2 g of O-ethyl S-propyl phosphorochloridodithioate was stirred for approximately 90 minutes. The salts were then removed by filtration and then filtrate concentrated under vacuum. The residual oil was dissolved in ether, the ether solution washed twice with 2 percent aqueous sodium hydroxide solution, once with saturated sodium chloride solution and was dried over anhydrous sodium sulfate. The ether was removed in a rotary evaporator leaving 10.3 g (94%) of a colorless oil. RI(25°)=1.5485.

Analysis: Found: C, 47.07; H, 6.32; N, 8.57. Calcd. for $C_{13}H_{21}N_2O_2PS_2$: C, 46.97; H, 6.37; N, 8.43.

Example 10

Phosphoramidothioic acid: (1-methylethyl), O-ethyl O-(2-(1-methylcyclopropyl)-5-pyrimidinyl) ester

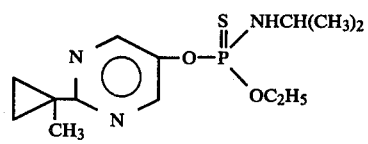

A mixture of 5.0 g of 2-(1-methylcyclopropyl)-5-pyrimidinol, 7 g of finely powdered potassium carbonate, 50 ml of acetonitrile and 6.7 g of phosphoramidochloridothioic acid: (1-methylethyl)-, O-ethyl ester was stirred for 90 minutes. The salts were then removed by filtration and the filtrate concentrated under vacuum. The residual oil was dissolved in ether, the ether solution washed twice with 2 percent aqueous sodium hydroxide, once with saturated sodium chloride solution and dried over anhydrous sodium sulfate. The ether was removed in a rotary evaporator leaving a colorless oil, RI(25°)=1.5274. Yield, 7.6 g (73%).

Analysis: Found: C, 49.52; H, 7.13; N, 13.48. Calcd. for $C_{13}H_{22}N_3O_2PS$: C, 49.51; H, 7.03; N, 13.32.

Example 11

Phenylphosphonothioic acid: O-methyl O-(2-(1-methylcyclopropyl)-5-pyrimidinyl) ester

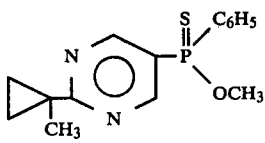

A mixture of 5.0 g of 2-(1-methylcyclopropyl)-5-pyrimidinol, 7 g of finely powdered potassium carbonate, 50 ml of acetonitrile and 6.8 g of O-methyl phenylphosphonochloridothioate was stirred overnight. The salts were then removed by filtration, the filtrate concentrated under vacuum, the residual oil dissolved in ether, the ether solution washed twice with 2 percent aqueous sodium hydroxide, once with saturated sodium chloride solution and dried over anhydrous sodium sulfate. The ether was removed in a rotary evaporator leaving a colorless oil. RI(25°)=1.5811. Yield, 7.55 g (75%).

Analysis: Found: C, 55.64; H, 5.59; N, 8.26. Calcd. for $C_{15}H_{17}N_2O_2PS$: C, 56.23; H, 5.35; N, 8.75.

Example 12

Ethylphosphonothioic acid: O-ethyl O-(2-(1-methylcyclopropyl)-5-pyrimidinyl) ester

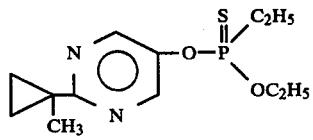

A mixture of 5.3 g of 2-(1-methylcyclopropyl)-5-pyrimidinol, 5.9 g of finely powdered potassium carbonate, 42 ml of acetonitrile and 6.7 g of O-ethyl ethylphosphonochloridothioate was stirred for three hours. The salts were then removed by filtration, the filtrate concentrated under vacuum, the residual oil taken in up ether, the ether solution washed twice with 2 percent aqueous sodium hydroxide, once with saturated sodium chloride solution and dried over anhydrous sodium sulfate. The ether was removed in a rotary evaporator leaving 9.1 g (93.8%) of a colorless oil, RI(25°)=1.5316.

Analysis: Found: C, 50.17; H, 6.67; N, 9.89. Calcd. for $C_{12}H_{19}N_2O_2PS$: C, 50.33; H, 6.69; N, 9.79.

The present novel compounds are useful for controlling most insects but are especially suitable for soil application due to the excellent stability in soil. These compounds have outstanding activity against western spotted cucumber beetle and corn rootworm.

Compositions comprising one or a mixture of the present pyrimidinyl phosphates, thiophosphates, dithiophosphates, amidothiophosphates or thiophosphonates as an active ingredient in association with various agricultural or pesticidal carriers, surface-active agents and other additaments are very useful for the control of corn rootworm. It is an advantage of the present invention that compositions containing the present compounds can be applied to soil in amounts required for corn rootworm control without significant injury to plant foliage.

In carrying out the method of the present invention, the corn rootworm can be controlled by contacting the corn rootworm, its habitat, and/or its food prior to ingestion, with a pesticidal amount of the unmodified pyrimidinyl phosphate, thiophosphate, dithiophosphate, amidothiophosphate or thiophosphonate. However, the present method also embraces the employment of a liquid, wettable powder, dust or granular composition containing the toxicant. Such compositions are adapted to be applied to living plants or to the locus thereof without substantial injury to the foliage or other parts thereof. In preparing toxicant compositions, the pyrimidinyl phosphate, thiophosphate, amidothiophosphate, thiophosphonate or dithiophosphate product can be modified with one or more of a plurality of adjuvants including aromatic solvents, petroleum distillates, surface-active dispersing agents, wettable powder, or finely divided inert solids, the latter as a dust or granule. Depending upon the concentration in the composition of the active product, such augmented compositions are adapted to be applied to corn rootworm, their habitats or their foods, or employed as concentrates and subsequently diluted with additional inert carrier to produce the ultimate treating compositions. In compositions to be employed as concentrates, the toxicant can be present in a concentration of from about 5 to about 98 percent by weight.

The exact concentration of the pyrimidinyl phosphate, thiophosphate, dithiophosphate, amidothiophosphate or thiophosphonate product employed in a composition for application to the pest, its habitat or food, can vary provided a pesticidal dosage of toxicant is supplied either on the pest or its environment or in its food. Good results are obtained with liquid compositions containing the active toxicant in the amount of, by weight, from about 0.5 to about 2000 parts or more per million, but preferably about 1 to about 400 ppm. Compositions containing as high as 90 percent by weight of toxicant are sometimes conveniently employed. With dusts and granules good results are obtained with compositions containing from about 0.05 to about 50 percent by weight, more preferably about 1 to about 20 percent by weight and most preferably about 2.5 to about 15 percent by weight of toxicant.

In the preparation of dust or granulated compositions, the pyrimidinyl phosphate, thiophosphate, dithiophosphate, amidothiophosphate or thiophosphonate compound can be compounded with any of the finely divided solids such as pyrophyllite, diatomaceous earth, gypsum and the like. In such operations, the finely divided carrier is ground or mixed with the toxicant or wet with a solution of the toxicant in a volatile organic solvent. Similarly, dust compositions containing one of these active compounds can be compounded from various of the solid surface active dispersing agents, such as fullers earth, attapulgite, bentonite and other clays. Depending upon the proportions of ingredients, these dust compositions can be employed as concentrates and subsequently diluted with additional solid surface active dispersing agent or with pyrophyllite, diatomaceous earth, gypsum and the like to obtain the desired amount of active ingredient in a composition adapted to be employed for the control of pests. Also such concentrate dust compositions can be dispersed in water, with or without the aid of dispersing agents, and wetting agents, to form spray mixtures.

Further, one of the present active compounds or a dust concentrate composition containing such compound can be incorporated in intimate mixture with surface active dispersing agents such as ionic and non-ionic emulsifying agents to form spray concentrates. Wherein such composition is a dust concentrate, it becomes a wettable powder when suitably formulated with emulsifying and/or wetting agents as understood in the art. Such concentrates are readily dispersible in liquid carriers to form sprays containing the toxicant in any desired amount. The choice of dispersing agent and amount thereof employed are determined by the ability of the agent to facilitate the dispersion of the concentrate in the liquid carrier to produce the desired spray composition.

While a composition of the toxicant in admixture with an inert or stabilized finely divided soil such as a montmorillonite clay may be granulated by well known methods to provide a granular product, it is preferred to provide a granulated solid carrier such as creekonite granules commercially prepared from a montmorillonite type clay, preferably containing a small amount of butyrolactone or stabilizer and to add the requisite amount of toxicant by spraying on toxicant, melted if necessary, or a solution of toxicant in a volatile solvent such as methylene chloride, as in a moving bed operation. The toxicant is imbibed by the granules. Any solvent present is removed in a drying operation. Preferred sized granules are about 24-48 mesh (sieve opening 0.7-0.295 mm).

The present active compounds can be compounded with a suitable water-immiscible organic liquid and surface active dispersing to produce emulsifiable liquid concentrates which can be further diluted with water to form spray mixtures in the form of oil-in-water emulsions. In such compositions, the carrier comprises an aqueous emulsion, that is, a mixture of water-immiscible solvent, emulsifying agent and water. Preferred dispersing agents to be employed in these compositions are oil soluble and include the non-ionic emulsifiers such as the polyoxyethylene derivatives of sorbitan esters, complex ether alcohols and the like. However, oil-soluble ionic emulsifying agents such as mahogany soaps or alkylbenzene sulfonates such as dodecylbenzene sulfonate or alkyl naphthaline sulfonates can also be used. Suitable organic liquids to be employed in the compositions include petroleum oils and distillates toluene, xylene, liquid halohydrocarbons, ketones and synthetic oils. Similarly, invert emulsions can be made and employed if desired.

When operating in accordance with the present invention, one of the present active compounds or a mixture thereof is applied to the corn rootworm to be controlled, to their habitat, including the soil or to their food, in any convenient fashion, for example by means of hand dusters or sprayers or by simple mixing with the food to be ingested by the pests. Applications to foliage of plants is conveniently carried out with power dusters, boom sprayers and spray dusters. In such foliar applications, the employed compositions should not contain any appreciable amounts of any phyto-toxic diluents or additaments. In large scale operations, dusts or low-volume sprays can be applied as from an airplane. Application to the soil is conveniently carried out with spray applicators including boom sprayers followed by working of the soil as with a disc harrow or other harrow. Soil application is also conveniently carried out at the time of planting by delivering composition in the form of a dust or granule into the seed furrow, or preferably by applying the granules in a band above the seed row usually with light soil incorporation.

For soil application, compositions containing the active toxicant are applied in an effective amount in the range of about 0.1 to about 5 pounds per acre, more preferably about 0.1 to about 2 pounds per acre. The most active toxicants amongst the present new compounds are effective at an application rate of about 1.0 pound per acre substantially without injury to growing crops.

The control of corn rootworm by the administration of the present novel active compounds is illustrated by the following examples.

Example 13

In separate operations, aqueous compositions of the present pyrimidinyl phosphate, thiophosphate, dithiophosphate, amidothiophosphate or thiophosphonate toxicant compounds are prepared as follows:

Four parts by weight of each respective toxicant compound, 0.08 part of sorbitan trioleate (Span* 85) and 0.02 part of a sorbitan monolaurate polyoxyethylene derivative (Tween* 80) are dispersed in 40 milliliters of acetone to produce a concentrate composition in the form of a water-dispersible liquid. This concentrate composition is dispersed in water to provide aqueous compositions containing varying amounts of the toxicant.
*Registered Trademark Also, the respective toxicant compounds are formulated in water with an alkyl aryl sulfonate (Nacconol* NR) and a substituted benzoid alkyl sulfonic acid (Daxad* No. 27) to produce aqueous compositions. In such operations, the materials are ballmilled together to produce compositions containing varying amounts of one of the toxicants, 300 parts by weight of Nacconol* NR and 300 parts by weight of Daxad* No. 27.
*Registered Trademark

Example 14

In test operations compositions are prepared according to the Span* 85 procedure of Example 13 containing, in each case, 400 ppm of the toxicant. In each case 75 gram portions of air-dried soil is treated with sufficient test composition, about 5 ml, to provide 25 ppm of toxicant in the soil after 25 hours of air drying. Each portion of treated soil is stirred until well mixed and divided and added to 2 vials previously infested with 50-100 western spotted cucumber beetles (*Diabrotica undecimpunctata undecimpunctata*) eggs. A grain of corn is planted in each vial and the vials watered and incubated in a warm humid environment. After 12 days the corn plants are rated for damage and any larvae present noted. The absence of larvae in the vials indicates 100 percent control.

Complete control was observed in tests employing the compounds of Examples 6 through 9.

Example 15

On repeating the tests of Example 14 at toxicant composition concentrations in the air dried soil of 6.25 and 1.5 ppm a number of the compounds of this invention were found to give complete control at toxicant compositions of less than 1.5 ppm.

The compounds act both systemically and as contact poisons to insects. It has been found that the compounds have good soil movement in that they need not be deposited immediately adjacent or on growing vegetation in order to provide protection from pests.

Those O,O-diethyl phosphorothioate compounds having 4 to 5 carbon atoms in the alkylcycloalkyl group constitute a preferred group to employ in the control of western spotted cucumber beetle and corn rootworm. They are characterized by having good soil stability and adequate residuality and in bringing about good grain crop increase in treated corn.

In another preferred group wherein R' is hydrogen, the compounds exhibit excellent activity against western spotted cucumber beetle. The most preferred compound is O,O-diethyl O-(2-(1-methylcyclopropyl)-5-pyrimidinyl)phosphorothioate.

We claim:

1. A compound having the formula:

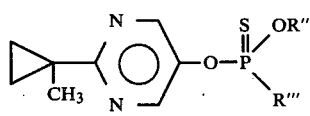

wherein R" is alkyl having 1 to 4 carbon atoms and R''' is alkyl of 1 to 2 carbons, alkoxy having 1 to 4 carbon atoms or phenyl.

2. The compound as in claim 1 wherein R" is ethyl.

3. The compound as in claim 2 wherein R''' is —OC$_2$H$_5$.

4. O,O-diethyl O-(2-(1-methylcyclopropyl)-5-pyrimidinyl)phosphorothioate.

5. A composition for controlling corn rootworm and western spotted cucumber beetle comprising an inert agricultural carrier in admixture with an insecticidally effective amount of a pyrimidinyl phosphate having the formula:

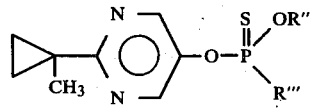

wherein R" is alkyl having 1 to 4 carbon atoms and R''' is alkyl of 1 to 2 carbons, alkoxy having 1 to 4 carbon atoms or phenyl.

6. The composition as in claim 5 wherein the carrier contains a surface active dispersing agent.

7. The composition as in claim 5 wherein the carrier is an inert solid and the composition is in granulated form.

8. The composition as in claim 5 wherein R" is ethyl.

9. The composition as in claim 8 wherein R''' is —OC$_2$H$_5$.

10. The composition as in claim 5 wherein the carrier contains a surface active dispersing agent.

11. The composition as in claim 5 wherein the carrier is an inert solid and the composition is in granulated form.

12. A method for controlling insects from the group consisting of corn rootworm and western spotted cucumber beetle which comprises applying to said insects, their habitats or food an insecticidally effective amount of a pyrimidinyl phosphate having the formula:

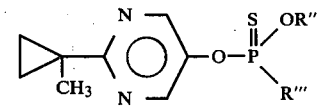

wherein R" is alkyl having 1 to 4 carbon atoms and R''' is alkyl of 1 to 2 carbons, alkoxy having 1 to 4 carbon atoms or phenyl in admixture with an inert agricultural carrier.

13. The method as in claim 6 wherein the compound is applied as an aqueous emulsion.

14. The method as in claim 6 wherein the compound is applied in the form of a granulated composition.

15. The method as in claim 14 wherein the granulated composition is applied to a crop selected from the group consisting of corn, sorghum, cotton and sugar beets.

16. The method as in claim 6 wherein R" is ethyl and R''' is —OC$_2$H$_5$.

17. The method as in claim 6 wherein the compound is admixed with an inert solid, the admixture is in granulated form and is applied to corn.

18. The method as in claim 6 wherein the compound is applied to corn rootworm or its habitat.

* * * * *

UNITED STATES PATENT AND TRADEMARK OFFICE
CERTIFICATE OF CORRECTION

PATENT NO. : 4,444,764   Page 1 of 2
DATED : April 24, 1984
INVENTOR(S) : Walter Reifschneider, Larry L. Larson It is certified that error appears in the above—identified patent and that said Letters Patent is hereby corrected as shown below:

In the Title Page, in the Abstract, Item (57), in the sixth line after the formulas, "1-alkylcycloalkyl" should read --2-alkylcycloalkyl--.
Column 2, line 64, "4-alkythio-" should read -- 4-alkylthio- --.
Column 3, line 66, "phosophorodichloridodithio" should read -- phosphorodichloridodithio --.
Column 5, line 19, "64.2 of" should read -- 64.2 g of --.
Column 6, line 33, "5" under the heading Example should read -- 8 --.
Column 6, line 48, the word "then" should read -- the --.
Column 7, lines 20-25, that portion of the formula reading

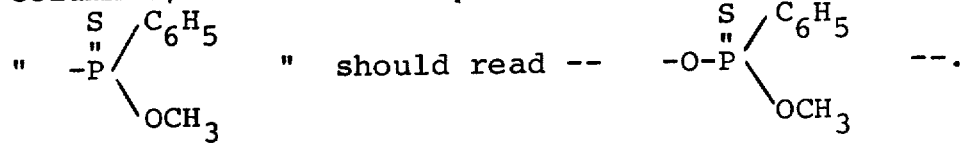

Column 7, line 58, "in up" should read -- up in --.
Column 12, lines 39, 41, 46, 48 and 51, each occurrence of "Claim 6" should read -- Claim 12 --.
Column 12, starting at line 53, a claim should be added as follows: --19. 2-(1-Methylcyclopropyl)-5-pyrimidinol. --.

UNITED STATES PATENT AND TRADEMARK OFFICE
CERTIFICATE OF CORRECTION

PATENT NO. : 4,444,764

DATED : April 24, 1984

INVENTOR(S) : Walter Reifschneider, Larry L. Larson

It is certified that error appears in the above-identified patent and that said Letters Patent is hereby corrected as shown below:

On the title page, column 2, after the Abstract,

"18 Claims, No Drawings" should read -- 19 Claims, No Drawings --.

Signed and Sealed this

Thirteenth Day of November 1984

[SEAL]

Attest:

GERALD J. MOSSINGHOFF

Attesting Officer

Commissioner of Patents and Trademarks